(12) United States Patent
Conteduca et al.

(10) Patent No.: US 7,989,518 B2
(45) Date of Patent: Aug. 2, 2011

(54) SYNTHETIC BIOCOMPATIBLE MATERIAL HAVING AN IMPROVED OXIDATION RESISTANCE, PROCESS FOR PREPARING THE SAME AND PROSTHETIC ARTICLES OBTAINED THEREFROM

(76) Inventors: Fabio Conteduca, Rome (IT); Fabio D'angelo, Pesche (IT)

( * ) Notice: Subject to any disclaimer, the term of this patent is extended or adjusted under 35 U.S.C. 154(b) by 0 days.

(21) Appl. No.: 12/373,765

(22) PCT Filed: Jul. 12, 2007

(86) PCT No.: PCT/EP2007/057209

§ 371 (c)(1),
(2), (4) Date: Jan. 14, 2009

(87) PCT Pub. No.: WO2008/006890

PCT Pub. Date: Jan. 17, 2008

(65) Prior Publication Data

US 2009/0281624 A1      Nov. 12, 2009

(30) Foreign Application Priority Data

Jul. 14, 2006    (IT) .................................. MI06A1375

(51) Int. Cl.
*A61F 2/02* (2006.01)
*C08K 5/45* (2006.01)
*C08K 5/36* (2006.01)

(52) U.S. Cl. ........................... 523/113; 524/84; 524/302
(58) Field of Classification Search .................. 523/113; 524/84, 111, 302; 623/11.11
See application file for complete search history.

(56) References Cited

U.S. PATENT DOCUMENTS

| 7,005,274 | B1 * | 2/2006 | Terkeltaub et al. | 435/29 |
| 2003/0212161 | A1 * | 11/2003 | McKellop et al. | 522/3 |
| 2007/0021496 | A1 * | 1/2007 | Terkeltaub et al. | 514/450 |
| 2007/0293647 | A1 * | 12/2007 | McKellop et al. | 526/352 |

FOREIGN PATENT DOCUMENTS

| WO | WO-01/20018 | 3/2001 |
| WO | WO-01/80778 | 11/2001 |
| WO | WO-2004/071496 | 8/2004 |
| WO | WO-2004/076289 | 9/2004 |

* cited by examiner

*Primary Examiner* — Kriellion A Sanders
(74) *Attorney, Agent, or Firm* — Connolly Bove Lodge & Hutz LLP

(57) ABSTRACT

Biocompatible material, in particular prosthetic material with improved resistance to oxidation, comprising UHMWPE and one or more antioxidants selected from the group consisting of lipoic acid, its analogs and derivatives, Vitamin C, coenzyme Q10, glutathione. It is also disclosed a process to prepare such material.

14 Claims, 3 Drawing Sheets

Figure 1:
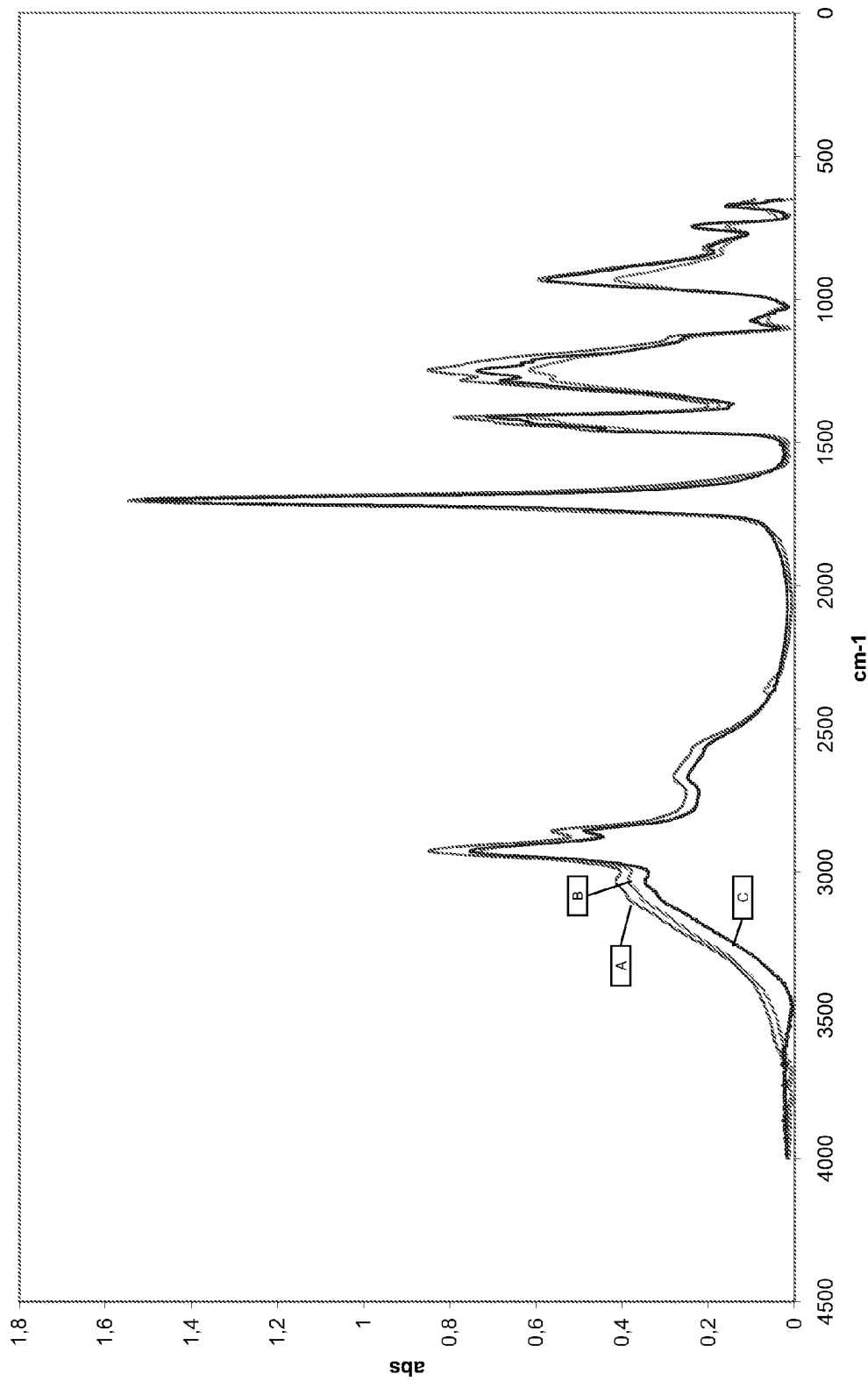

SYNTHETIC BIOCOMPATIBLE MATERIAL HAVING AN IMPROVED OXIDATION RESISTANCE, PROCESS FOR PREPARING THE SAME AND PROSTHETIC ARTICLES OBTAINED THEREFROM

CROSS REFERENCE TO RELATED APPLICATIONS

This application is a national phase of PCT/EP2007/057209, filed on Jul. 12, 2007, which claims priority to Italian Patent Application No. MI 2006 A 001375, filed on Jul. 14, 2006, the entire contents of which are incorporated herein by reference in their entireties.

The present invention relates to a synthetic biocompatible material having improved oxidation resistance, to a process for preparing the same, and to shaped articles obtained therefrom.

The invention refers particularly to a synthetic material having improved oxidation resistance, comprising a biocompatible polymer with high molecular weight and one or more antioxidant substances with high biocompatibility as additives for the biocompatible polymer. The invention refers more particularly to a prosthetic material comprising Ultra High Molecular Weight Polyethylene (UHMWPE) and one or more antioxidant substances with high biocompatibility.

Polyethylene (PE), particularly UHMWPE, is a polymeric biocompatible material that has been used in joint replacements for a long time. After an initial enthusiasm for the good results achieved, in more recent years the large use of UHMWPE has shown unexpected problems. The international literature frequently reports failures of joint replacements due to wear of UHMWPE in hip and knee prosthesis.

Therefore, it is broadly recognised by the international scientific community that the life of prosthetic implants depends mainly on the degradation of the polyethylene component. In fact, the particulate wear deriving from the degradation of the polyethylene component is responsible for inflammation and synovial reaction that bring about phenomena of aseptic mobilisation and consequent clinical failure of the prosthesis.

Several methods have been studied to improve the polyethylene behaviour with respect to degradation, with some recent improvements in mechanical properties. Fully satisfactory results, however, have not been obtained yet. The two most important problems not completely resolved are:
1) oxidation, associated to the process of aging of polyethylene, that inevitably leads to a decay of its chemical properties,
2) wear, namely the process of releasing small particles of polyethylene, which are responsible for inflammations, synovial reaction and prosthesis aseptic mobilisation, as described above.

As it is well known to the skilled person, the process of oxidation of plastic materials occurs also in UHMWPE. Such process reduces progressively the mechanical resistance of prosthetic inserts and increases the wear particulate, causing a mobilisation of the prosthesis, de-lamination and breaking of the joints. Oxidation is a continuous and inexorable process that involves all the materials in contact with oxygen. In joint replacements, the carriers of oxygen are blood and the biological liquids that enter into contact with the prosthetic components of the implant, thus with polyethylene.

Although it is a well known process, attention has been paid to oxidation also recently since oxidation is closely related to the type of sterilisation that is performed on the PE. Methods of sterilisation currently employed are:

1) treatment with ethylene oxide (chemical reaction that brings about a surface sterilisation, but does not change the chemical properties of PE).
2) irradiation with gamma rays and accelerated electrons (surface and in-depth interaction that changes the chemical properties of PE).

Currently most of UHMWPE manufacturers carry out sterilisation by gamma rays since the interaction of gamma rays with PE promotes the process of cross-linking, namely the formation of transversal links between linear polymer chains, which make the material more resistant to wear stress. Cross-linked PE is therefore more resistant to wear stress but is also more quickly oxidised, since the creation of cross-links between linear chains creates also free radicals which react with oxygen and speed up the UHMWPE oxidation process. For that reason the material is typically preserved and sold in vacuum packages, to avoid or limit contact with air. However, oxidation can be delayed but not avoided, since an implanted prosthesis comes into contact with organic liquids that carry oxygen and promote oxidation. Oxidative degradation of UHMWPE caused by gamma-sterilisation in air to a dose of 25-37 kGy leads to embrittlement and de-lamination wear in tibial components of total knee replacement prostheses and accelerated particulate wear in acetabular cups of total hip replacement prostheses. Therefore, an ideal material to manufacture a prosthesis would be a cross-linked PE, which is more wear resistant, but at the same time resistant to the oxidation process. For that reason it has been described in the literature the introduction into UHMWPE of an antioxidant that is able to prevent oxidation, in particular Vitamin E, which is lipophilic and liposoluble, thus it can migrate inside PE. Moreover, it is a biocompatible substance produced in the human body. Relevant articles are:

Oral E, Wannomae K K, Rowell S L, Muratoglu O K; Migration stability of α-tocopherol in irradiated UHMWPE; Biomaterials 27 (2006) 2434-2439;

Oral E, Greenbaum E S, Malhi A S, Harris W H, Muratoglu O K; Characterisation of irradiated blends of α-tocopherol and UHMWPE; Biomaterials 26 (2005) 6657-6663;

Shibata N, Yomita N; The anti-oxidative properties of α-tocopherol in γ-irradiated UHMWPE with respect to fatigue and oxidation resistance; Biomaterials 26 (2005) 5755-5762;

Oral E, Wannomae K K, Hawkins N, Harris W H, Muratoglu O K; α-Tocopherol-doped irradiated UHMWPE for high fatigue resistance and low wear; Biomaterials 25 (2004) 5515-5522;

Renò F, Bracco P, Lombardi F, Boccafoschi F, Costa L, Cannas M; The induction of MMP-9 release from granulocytes by vitamin E in UHMWPE; Biomaterials 25 (2004) 995-1001.

Vitamin E can be introduced in the PE in two ways: 1) mixed with the pure polymer in the granular form or powder form; 2) introduced by various methods into a pre-moulded PE article. Both methods have already had the approval of the American Food and Drug Administration.

Although the first studies on this material have shown a good effect of Vitamin E in terms of reduction of oxidation, the body answer to contact with Vitamin E and the behaviour of Vitamin E inside the PE are still rather unknown. It is believed, however, that wearing of the PE causes that a small amount of Vitamin E is inevitably released in the joint. Since Vitamin E is liposoluble, it does not dissolve in the synovial liquid, and it cannot be drained by the lymphatic system, therefore it likely forms some deposits inside the joint.

Therefore the need is felt for a prosthetic material with improved resistance to oxidation, which is also easily processable into a prosthesis and remains unchanged for long time once the prosthesis has been implanted in the body.

These and other objects of the invention are achieved with a biocompatible material with improved resistance to oxidation, comprising a synthetic polymer and one or more antioxidant substances selected from the group consisting of lipoic acid and its analogs and derivatives as defined by the general formula (I), Vitamin C, coenzyme Q10, and Glutathione.

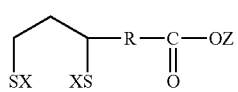

(I)

where:
X=H; or —X—X— is covalent bond linking the S atoms;
R=$C_{1-16}$ alkylene o alkenyl substituted or not;
Z=H, halogen, $C_{1-10}$ alkyl;

More particularly, the invention refers to prosthetic material with improved resistance to oxidation comprising a high molecular weight olefin polymer, preferably Ultra High Molecular Weight Polyethylene (UHMWPE).

The invention refers also to the use of one or more antioxidant substances with high biocompatibility selected from the group consisting of lipoic acid and analogs and derivatives thereof as defined by the general formula (I), Vitamin C, Coenzyme Q10, and glutathione, as additives for the biocompatible material.

According to an aspect of the invention, the biocompatible material is used to manufacture a prosthesis, and the invention refers also to a prosthesis obtained by from said biocompatible material.

The invention refers also to a process for the preparation of a biocompatible material with improved resistance to oxidation comprising a synthetic polymer and one or more antioxidant substances selected from the group consisting of lipoic acid and analogs and derivatives thereof as defined by the general formula (I), Vitamin C, coenzyme Q10, and glutathione.

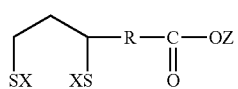

(I)

where:
X=H; or —X—X— is a covalent bond between the S atoms;
R=$C_{1-16}$ alkylene or alkenyl, substituted or not;
Z=H, halogen, $C_{1-10}$ alkyl;
characterised in that one or more of said antioxidant substances is mixed with granules of said synthetic polymer in an effective amount before melting said polymer and forming a shaped article.

According to another aspect of the invention, the shaped article formed by the process above is a prosthetic article.

With respect to manufacturing a prosthetic article, the antioxidant substances according to the invention can be introduced into a pre-formed prosthetic insert by a process characterised by immersing the insert in a solution of a solvent for the antioxidant substance at a suitable temperature and for a suitable time, so as to allow migration of the substance into the synthetic polymer. In an embodiment of this process a pre-formed insert made of UHMWPE is immersed in a saturated solution of ethyl alcohol and antioxidant substance at a relatively high temperature but lower than the melting temperature of UHMWPE, at a pressure above atmospheric pressure, for a sufficient time.

The invention discloses to improve the resistance of a prosthetic material, therefore to reduce the oxidation, particularly of PE, by adding to such material an anti-oxidant substance that is biocompatible, liposoluble and also water soluble at the same time, thus capable of being introduced in the PE and then absorbed by the synovial cells membrane and by lymphatic system.

The preferred anti-oxidant substance is lipoic acid (LA) or its analogs and derivatives, which fulfil both the requirements above. Further, lipoic acid it is a substance produced by the human body itself.

Lipoic acid (LA) is a molecule containing sulphur having formula $C_8H_{14}S_2O_2$. Dihydrolipoic acid (DHLA) is a lipoic acid derivative and it is possible to convert one into the other by typical redox reactions. Lipoic acid exists in two enantiomeric forms, R and S. The natural form (R-enantiomer) is the biologically active one, while the synthetic lipoic acid is a mixture of the R and S forms. The present invention pertains to both forms (R and S). A unique feature of this anti-oxidant is that of being liposoluble and hydrosoluble (water soluble) at the same time. Lipoic acid form chelates, namely can "capture" metal cations, inactivating their toxic effect.

Lipoic acid plays a major role in cells methanolism in most living organisms, from bacteria to humans. Antioxidant power of lipoic acid is well known. For this reason lipoic acid can be taken as food supplement, and is effective in performing functions of vital importance for the organism.

Lipoic acid is a relatively small molecule, formed by a chain of 8 carbon atoms and 2 sulphur atoms in the ends. In the reduced form, also known as dihydrolipoic acid, the S atoms are present as free thiols (—SH), while in the oxidised form, thanks to the generation of a disulphur bonds (—S—S—), have a terminal ring structure. Lipoic acid can thus undergo redox reactions, act as carrier for electrons or acetyl group or, generally, for acilic groups. For this reason alpha-lipoic acid acts a cofactor for numerous enzymes involved in the conversion process of glucose, fatty acids and other sources of energy in adenosine trifosfate (ATP), e.g. piruvate dehydrogenase, alpha-ketoglutarate dehydrogenase. Such process takes place in cells mitochondrion and comprises a complex set of reactions known as "Krebs cycle". The availability of lipoic acid in cells enhances the effectiveness of the Kerbs cycle and the effectiveness of the entire process.

Besides being an antioxidant, alph-lipoic acid possesses unique features that make it necessary to our organism to limit damages caused by free radicals, such as:

a) High absorbibility: being a relatively small molecule, alpha-lipoic acid is readily absorbed and transported through cell membranes, where it can exert its action;

b) Versatility: alpha-lipoic acid is active both in aqueous cell portions (cytoplasm) and in lipidic cell portions (cell membrane);

c) Antioxidant power in both forms: the reduced form (acid dihydroxy lipoic) is more active, but also the oxidised form retains antioxidant properties;

d) Broad spectrum of action: DHLA is active against many radicals, e.g. peroxy, hydroxy, nitric-peroxy, and superoxides and hydroperoxy;

e) Strenghtening and completing the defensive network performed by other antioxidants: LA in the reduced form (DHLA) can donate electrons to oxidised and not active forms of glutathione (glutathione disulfide) and vitamin C (dehydroascorbic acid), which converts them to reduced glutathione and ascorbic acid, respectively. In turn, vitamin C in reduced form can re-activate the oxidised form of vitamin E by reducing it to tocopherol (active vitamin E). This process is cyclic. After donation of electrons, DHLA acid returns to the oxidised form of LA. Since also LA in oxidised form has antioxidant power, the regeneration cycle continues to the benefit of cells;

f) Control of release of free radicals due to accelerated energy methanolism: methanolisation of energy through accelerated Krebs cycle promotes the formation of free radicals. Although most of them take part in the set of chemical reactions of the energetic methanolism, some radicals may be released and gradually cause damages to cells. Availability of LA, although enhancing the Krebs cycle and the related energy balance, enhances also a control of free radicals formed during the entire process. In this way a sufficient protective action is ensured, even if the energy balance is high.

Dosage and Toxicity

LA is usually present in significant amounts in mitochondria-rich tissues, i.e. in those organelles that provide cells with energy. LA is present in leaves of plants that contain mitochondria and in non-photosynthetic vegetable tissues, such as potato bulbs. Spinach and broccoli are LA rich as well, but the major source of LA is read meat, in particular the heart. Although LA cannot be defined an essential element, since our organism can synthesize it, it is present in relatively small amounts in human body. LA can thus be advantageously taken as a food supplement. Dosage can vary depending on each individual, life style, physical activity, exposure to sun rays, and diet.

A suggested dosage to prevent damages caused by free radicals in healthy subjects is 50 mg/day, to be taken preferably in association with other antioxidant substances such as vitamin A, C, E, Selenium, Coenzyime Q10.

With respect to toxicity, there has been no side effect reported for a dose of 50 mg/day of LA. Some studies on dosages of from 100 to 600 mg/day of LA for periods of from 3 to 6 months have shown a low toxicity on human beings. Other studies have shown that there is no mutagenity or teratogenity or cancerogenity associated to LA.

Formulae of LA and DHLA are shown below in a redox scheme:

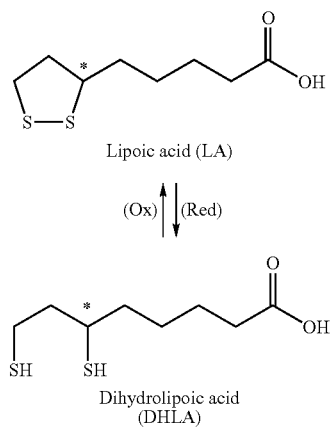

Lipoic acid (LA)

(Ox) ↑↓ (Red)

Dihydrolipoic acid (DHLA)

With reference to general formula (I), LA is obtained when:
—X—X— is a covalent bond linking the S atoms;
R=unsubstituted $C_4$ alkylene;
Z=H With reference to general formula (I), DHLA is obtained when:
X=H;
R=unsubstituted $C_4$ alkylene;
Z=H This invention concerns the introduction of one or more substances selected from the group consisting of LA or DHLA in any natural or synthetic form, including their analogs and derivatives, of Vitamin C, of the Q10 coenzyme, and of the glutathione in any plastic materials, preferably in Ultra High Molecular Weight Polyethylene (UHMWPE) to produce a material suitable for the manufacture of prosthetic material having improved oxidation resistance.

Lipoic acid can be mixed with UHMWPE in granular or pelletized form. LA is mixed in any desired amount with UHMWPE before moulding it into a shaped article. The presence of the anti-oxidant does not interfere with the process of manufacturing a shaped article, and it does not change the moulding temperature and the pressure. Differently from other antioxidants which are available only in a viscous liquid form, such as vitamin E, lipoic acid can be mixed with UHMWPE without using any solvent or diluent, which could remain present as impurity in the polymer.

Lipoic acid can also be introduced into the pre-moulded PE by putting into contact a suitable amount of LA in powder form with UHMWPE, then heating the two materials at a temperature at which LA melts but that is below the melting temperature of UHMWPE. This process is carried out at the atmospheric pressure and/or at higher pressures, using suitable equipment. Since the melting temperature of Lipoic Acid is lower than that of UHMWPE, the Lipoic acid melts and penetrate as a lipophilic liquid into the plastic material. Being water-soluble and liposoluble, the LAc can penetrate into the UHMWPE as such and/or with a carrier (alcohol).

The anti-oxidant properties of LA are well known, but it also has a synergistic action with other anti-oxidants, such as Vitamin E. Therefore a mixture of Lipoic Acid with other anti-oxidants (e.g. Vitamin E) can be advantageously used according to the invention.

The process of manufacturing a prosthetic material comprising UHMWPE and LA and Vitamin E can be carried out in two ways:
1) Diluting Vitamin E and Lipoic Acid in a liquid carrier liquid (e.g. alcohol), putting into contact the diluted substances with UHMWPE to effect a migration of the substances into the UHMWPE mass, at a suitable temperature and pressure, evaporating the liquid carrier;
2) First introducing LA into UHMWPE according to any process described above, then introducing Vitamin E into the material by diluting it as described under paragraph a) above. Any such process can be implemented before or after the gamma sterilisation treatment.

EXAMPLES

UHMWPE GUR 1050 (Ticona Inc, Bayport, Tex., USA) in powder form was mixed with 0.5 weight % of Lipoic Acid in powder form (Talamonti, Italy, stock n. 1050919074). The mixture was then moulded in a cell at 160° C. and at a pressure of 200 MPa.

A comparative sample was made with the same UHMWPE GUR 1050 only, namely without mixing it with lipoic acid.

Each sample of UHMWPE, virgin and doped with lipoic acid, was gamma irradiated to a dose of 30 kGy (Isomedix, Northborough, Mass.), then was processed into cylindrical pins of 20 mm length and 9 mm diameter.

Each sample, virgin and doped, was then aged at 80° C. in a convection oven for 5 weeks, in air (ASTM standard F2003-02). After aging and oxidation, thin sections of 100-200 mm thickness of each sample were prepared using a Leitz Wetzlar Sledge Microtome (Leica, Nussloch, Germany). The irradiated and aged sections of cylindrical pins samples were then analysed by means of Fourier Transform Infrared Spectroscopy (FTIR). The IR analysis was performed using a Nicolet Magna 860 spectrometer.

The samples above were used to investigate thermal stability and oxidation stability.

Thermal Stability

The purpose of these examples was to investigate the presence and stability of Lipoic Acid inside UHMWPE with which it was pre-mixed.

UHMWPE commonly melts at 138° C., but Lipoic Acid melts at about 65° C. Therefore, to check the Lipoic Acid stability into the UHMWPE at high temperatures a Lipoic Acid-doped UHMWPE was tested at 150° C. and 200° C.

The results are shown in FIG. 1, which shows FTIR spectra of pure Lipoic Acid (line A), and mixtures of UHMWPE with 0.5% wt of lipoic acid at different temperatures. Line B represents the spectrum of UHMWPE doped with LA, heated at 150° C. for 2 hours, then cooled at room temperature, in which the spectrum of pure UHMWPE was detracted as baseline. Line C represents the spectrum of UHMWPE doped with LA, heated at 200° C. for 24 hours, then cooled in which the spectrum of pure UHMWPE was detracted as baseline, as for line B. It appears from FIG. 1 that the stability of Lipoic Acid is substantially unchanged despite the thermal treatment at the temperatures of 150 and 200° C.

Oxidation Stability

Figure 2:
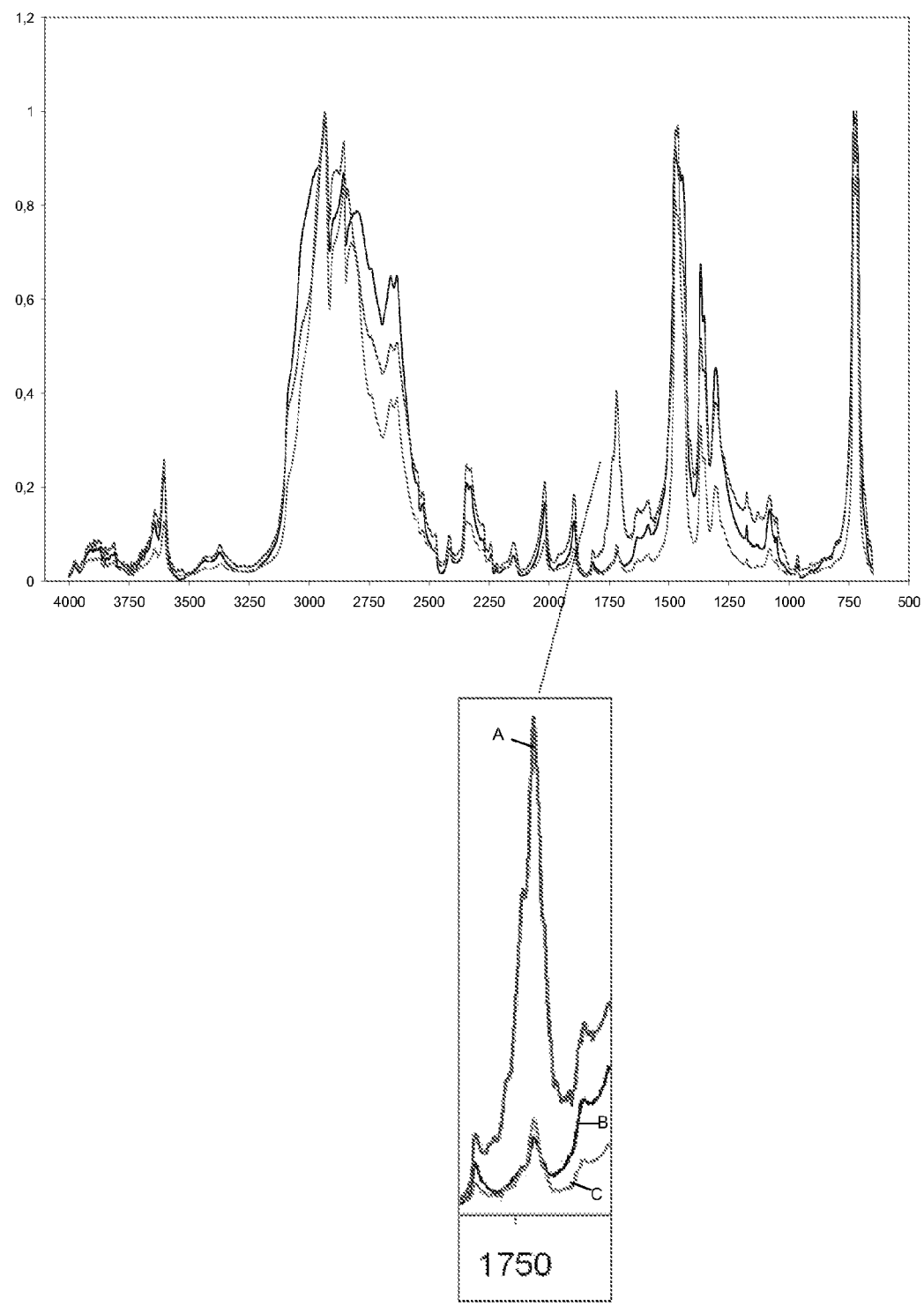
Figure 3:
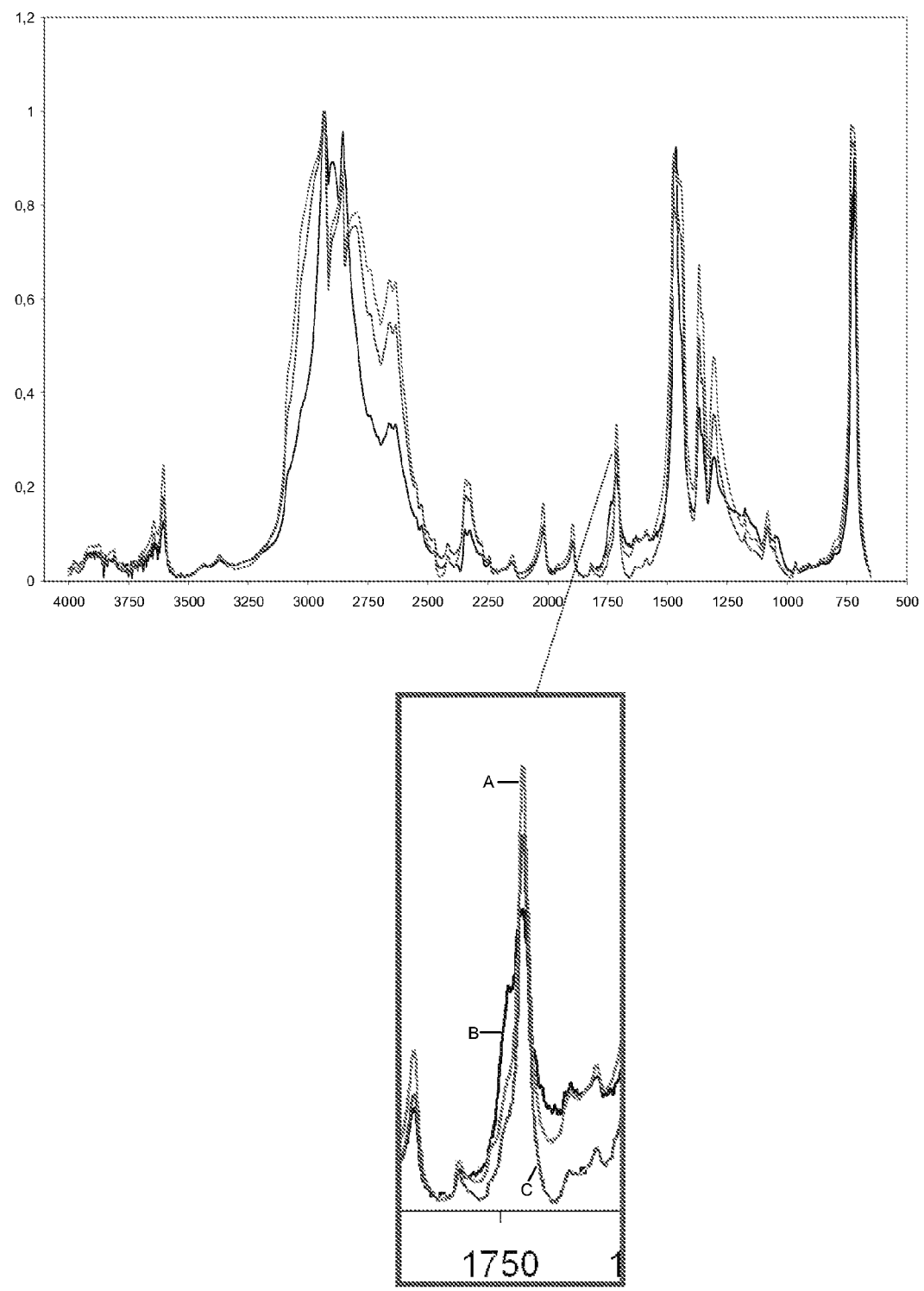

The effect of aging on the oxidation of virgin UHMWPE and UHMWPE doped with lipoic acid is shown in FIG. 2 and FIG. 3, respectively. An oxidation index OI was defined as the ratio of the area under 1740 cm$^{-1}$ carbonyl and 1370 cm$^{-1}$ methylene absorbance peaks. Each figure shows spectra related to the surface of the sample and at different depths inside the sample. The peak at 1740 cm$^{-1}$ shows products of oxidation of UHMWPE, but also detects the presence of the carbonyl group of lipoic acid. However, lipoic acid is present at any level of depth in the doped UHMWPE sample, therefore it does not affect the investigation on oxidation of UHMWPE material at the same levels of depth.

FIG. 2 shows a very high oxidation index on the surface of pure UHMWPE (line A), which decreases at the depth of 1500 and 3000 micron (line B and C, respectively). This is consistent with recent studies that show a zero oxidation index beyond a depth of 1500 micron, and with the finding that oxygen cannot go deeper than 1500 micron.

FIG. 3 shows that the oxidation index of doped UHMWPE does not change from the surface to the depth. This shows that there is substantially no oxidation of UHMWPE. As discussed with reference to FIG. 2 above, it can be assumed that beyond 1500 micron there is no oxidation. Since the 3 curves A, B, and C of FIG. 3 substantially overlap, and assuming that the curves B and C do not reveal any oxidation of UHMWPE index around zero because there is no oxidation at 1500 and 1700 micron, then also curve A (the surface curve) does not show any oxidation of UHMWPE.

The examples above show that lipoic acid is effective as antioxidant and is stable with respect to thermal treatment.

The biocompatible material according to the invention finds application also to manufacture articles other than prosthetic articles, for example in the field of processing or packaging food, beverages, pharmaceutical products, medicines, and the like, regardless of whether such articles require sterilisitaion or irradiation.

The invention claimed is:

1. Biocompatible material with improved resistance to oxidation, comprising a high molecular weight olefin polymer and one or more antioxidants selected from the group consisting of: lipoic acid and its analogs and derivatives as defined by the general formula (I);

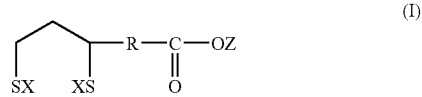

where:
X=H; or —X—X— is covalent bond linking the S atoms;
R=C1-16 alkylene or alkenyl, substituted or not;
Z=H, halogen, $C_{1-10}$ alkyl.

2. Biocompatible material according to claim 1, characterised that said synthetic polymer is Ultra High Molecular Weight Polyethylene (UHMWPE).

3. Biocompatible material according to claim 1, characterised that said antioxidant is selected from the group consisting of lipoic acid and dihydroxylipoic acid.

4. Prosthetic article characterised by comprising a biocompatible material according to claim 1.

5. Process for the preparation of a biocompatible material according to claim 1, characterised by mixing an effective amount of one or more of said antioxidants with said high molecular weight olefin polymer before melting said polymer, then forming a shaped article.

6. Process for the preparation of a biocompatible material according to claim 1 wherein said high molecular weight olefin polymer is UHMWPE, characterised by contacting a pre-formed article of UHMWPE with a solution of said antioxidant to allow migration of said antioxidant into said UHMWPE, said contacting being carried out at a temperature above room temperature and below the melting temperature of said UHMWPE, and at a pressure above atmospheric pressure.

7. Process for the preparation of a biocompatible material according to claim 1 wherein said high molecular weight olefin polymer is UHMWPE, characterised by contacting UHMWPE with said antioxidant in powder form, heating said antioxidant to a temperature above its melting temperature and below the melting temperature of said UHMWPE, and at a pressure above atmospheric pressure, to allow migration of said antioxidant in a molten sate into said UHMWPE.

8. Shaped prosthetic article manufactured by using a biocompatible material obtained by the process according to claim 6.

9. A method of manufacturing a prosthetic article which comprises shaping the biocompatible material according to claim 1.

10. A method of manufacturing a prosthetic article which comprises shaping the biocompatible material according to claim 2.

11. A method of manufacturing a prosthetic article which comprises shaping the biocompatible material according to claim 3.

12. Prosthetic article characterised by comprising a biocompatible material according to claim 2.

13. Shaped prosthetic article manufactured by using a biocompatible material obtained by the process according to claim 5.

14. Shaped prosthetic article manufactured by using a biocompatible material obtained by the process according to claim 7.

* * * * *